(12) United States Patent
Wiser et al.

(10) Patent No.: US 10,937,533 B1
(45) Date of Patent: Mar. 2, 2021

(54) LOCALIZED LEARNING OF MEDICATION ROUTINE

(71) Applicant: Verily Life Sciences LLC, Mountain View, CA (US)

(72) Inventors: Robert Wiser, San Francisco, CA (US); Ryan Kramer, San Francisco, CA (US); Andrew Reusch, San Francisco, CA (US); Grant Smith, Belmont, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 161 days.

(21) Appl. No.: 16/190,539

(22) Filed: Nov. 14, 2018

Related U.S. Application Data

(60) Provisional application No. 62/587,295, filed on Nov. 16, 2017.

(51) Int. Cl.
| | | |
|---|---|---|
| *A61J 7/04* | (2006.01) | |
| *G16H 20/13* | (2018.01) | |
| *B25J 9/16* | (2006.01) | |
| *G05B 13/02* | (2006.01) | |

(52) U.S. Cl.
CPC ........... *G16H 20/13* (2018.01); *A61J 7/04* (2013.01); *B25J 9/163* (2013.01); *G05B 13/0265* (2013.01)

(58) Field of Classification Search
CPC ...... A61J 7/049; A61J 7/0427; A61J 2200/30; G07F 17/0092; G06F 19/3462; G06F 19/3468; B25J 9/163; G05B 13/0265
See application file for complete search history.

(56) References Cited

U.S. PATENT DOCUMENTS

| | | | |
|---|---|---|---|
| 2009/0050645 A1* | 2/2009 | Burg | G07F 9/002 221/15 |
| 2010/0164716 A1* | 7/2010 | Estevez | A61J 7/0445 340/540 |
| 2012/0247478 A1* | 10/2012 | Harrington | A61M 16/0825 128/207.14 |
| 2015/0066429 A1* | 3/2015 | Nielsen | A61J 1/00 702/177 |
| 2017/0018166 A1* | 1/2017 | Johnson | G08B 13/08 |

* cited by examiner

*Primary Examiner* — Timothy R Waggoner
(74) *Attorney, Agent, or Firm* — Perkins Coie LLP

(57) ABSTRACT

A medication dispenser apparatus is described. The apparatus includes a container configured to hold medication, a display interface, and a controller configured to perform, in sequence, a learning operation in which the controller learns a medication dispensing regimen of the container, a validation operation in which the controller validates the learned medication dispensing regimen; and a notification operation in which the controller provides on the display interface a status of use of the container for medication dispensing in relation to the learned medication dispensing regimen.

16 Claims, 5 Drawing Sheets

LOCALIZED LEARNING OF MEDICATION ROUTINE

CROSS-REFERENCE TO RELATED APPLICATION

This application claims priority to U.S. Provisional Application Ser. No. 62/587,295, filed Nov. 16, 2017 which is incorporated by reference herein in its entirety.

TECHNICAL FIELD

Various embodiments concern techniques for monitoring medication dispensing.

BACKGROUND

Prescriptions are routinely filled by providing medication to patients in pill bottles. In some cases, a patient may need to take a medication at a regular frequency. The patient may, however, not adhere to such a schedule for several reasons. In such cases, a caregiver does not have a way to know whether or not the medication was consumed by the patient according to the prescribed schedule.

SUMMARY

The present document discloses techniques that may be used in embodiments of a medication dispenser apparatus in which the apparatus learns medication regimen of a patient. The learned regimen may be used for monitoring future adherence to the regimen.

In one example aspect, a medication dispenser apparatus is disclosed. The apparatus includes a container configured to hold medication, a display interface and a controller. The controller is configured to perform, in sequence, a learning operation in which the controller learns a medication dispensing regimen of the container, a validation operation in which the controller validates the learned medication dispensing regimen; and a notification operation in which the controller provides on the display interface a status of use of the container for medication dispensing in relation to the learned medication dispensing regimen.

In another example aspect, a processor implemented method is disclosed. The method includes learning, during a first time period having a first duration, a medication dispensing pattern of a pill bottle, validating, during a second time period having a second duration, a result of the learning, and notifying, during a third time period subsequent to the second time period, status of pill bottle usage with respect to the result of the learning.

In another example aspect, an apparatus comprising a microprocessor is disclosed. The microprocessor is configured to operate in a first state during which the microprocessor learns a medication dispensing regimen of a pill bottle, a second state during which the microprocessor validates the learned medication dispensing regimen using medication dispensing events of the pill bottle, and a third state during which the microprocessor indicates, on a display interface, a current status of usage in relation to the learned medication dispensing regimen.

These, and other, aspects are described throughout the present document.

BRIEF DESCRIPTION OF THE DRAWINGS

Various features and characteristics of the technology will become more apparent to those skilled in the art from a study of the Detailed Description in conjunction with the drawings. Embodiments of the technology are illustrated by way of example and not limitation in the drawings, in which like references indicate similar elements.

Figure 1:
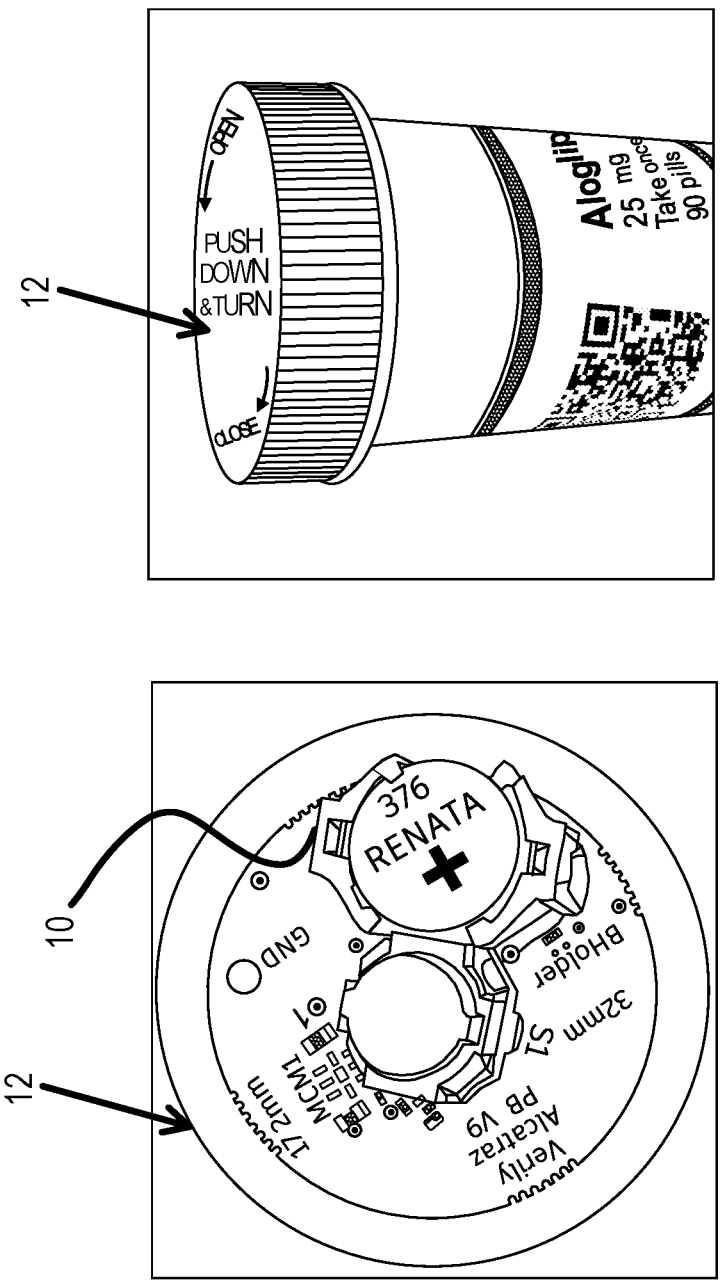
FIG. 1 shows an example of a medication dispensing pill bottle and a cap that includes a connectivity module.

The drawings depict various embodiments for the purpose of illustration only. Those skilled in the art will recognize that alternative embodiments may be employed without departing from the principles of the technology. Accordingly, while specific embodiments are shown in the drawings, the technology is amenable to various modifications.

DETAILED DESCRIPTION

Medical practitioners routinely prescribe medications to patients and provide dose guidelines about how often and in what amount to consume the medication. Monitoring and reporting whether a patient is abiding the medication consumption schedule is beneficial for a patient's health, both in terms of bringing about the intended healing and also avoiding other complications due to over or under consumption of medication.

Due to mental or physical limitations, patients sometimes may not be able to remember and record their medication use. To assist patients with consumption of the right amount of medication at the right time, pill dispensing technologies have been developed including color coded dispensing and pill organizers that hold pills in separate compartment on a per-day or per-dose basis.

One disadvantage of such dispensers and pill organizers is that while total amount of pills taken from the dispenser can be seen, there is no record of whether these pills were consumed at the recommended dosage and frequency.

Some pill dispenser may use electronics to monitor pill dispensing. However, such solutions require frequent replacement or recharging of batteries and are susceptible to inaccuracy when battery runs out. Furthermore, such implementations may have to be programmed with the medication regimen or the dispensing pattern to be monitored to check for adherence. This introduces an additional step in an already busy pharmacist's workflow of filling prescriptions.

In some existing systems, a usage regime is pre-programmed into a device. This requires the device to have reception capability in operation. Such designs therefore use additional overheads of the infrastructure that goes around the programming step and also increases the power consumed by the device during operation to be able to receive signals.

The technology described in the present document can be used in various embodiments to solve these problems, and others.

In some embodiments, the pill bottle may be configured to learn a user's medication regimen based on time profile of the pill bottle being opened for medication dispensing. Thereafter, adherence to the medication taking regimen may be monitored. A visual indication, e.g., using LEDs, may be provided to the user to indicate whether or not a medical regimen learned by the pill bottle is being adhered to.

Alternatively, or in addition, the monitored usage data may be transmitted to a companion device.

For example, in some embodiments, Bluetooth Low Energy (BLE) wireless technology may be used to transmit the compliance information to a user device such as a smartphone or a computer so that the user device may display the information to a caregiver or the patient.

In some embodiments, a connectivity module is designed to fit within a standard prescription pill bottle cap and contains one or more of the following features and functionalities:

1) Sensor for detecting when the bottle has been opened. The sensor may be, for example, a pressure-sensitive switch.

2) A memory for storing of a log of openings.

3) BLE transmit-only module for broadcasting ID and usage logs.

4) Multi-colored (e.g., RGB) or blinkable LED to provide visual feedback to users.

5) A Microcontroller to control the behavior of the system.

In some embodiments, the device is implemented to have a transmit-only functionality. Therefore, the device will not be capable of being reprogrammed after manufacturing, either wirelessly or via electrical connection. Since medication regimes (i.e. frequency and cadence of dosing) vary by medication and patient, and because patients make their own routines (e.g. taking a daily mediation in the morning v. taking it before bed). The bottle therefore may implement a way to determine the usage regime, and to adjust he corresponding feedback behavior accordingly.

FIG. 1 shows an example of a prototype circuit for implementing some of the techniques described herein. On the left is an example of a connectivity module 10 affixed to the cap 12 (in a flipped view) and on the right is an example of a medication bottle, including the cap 12 in closed position.

Figure 2:
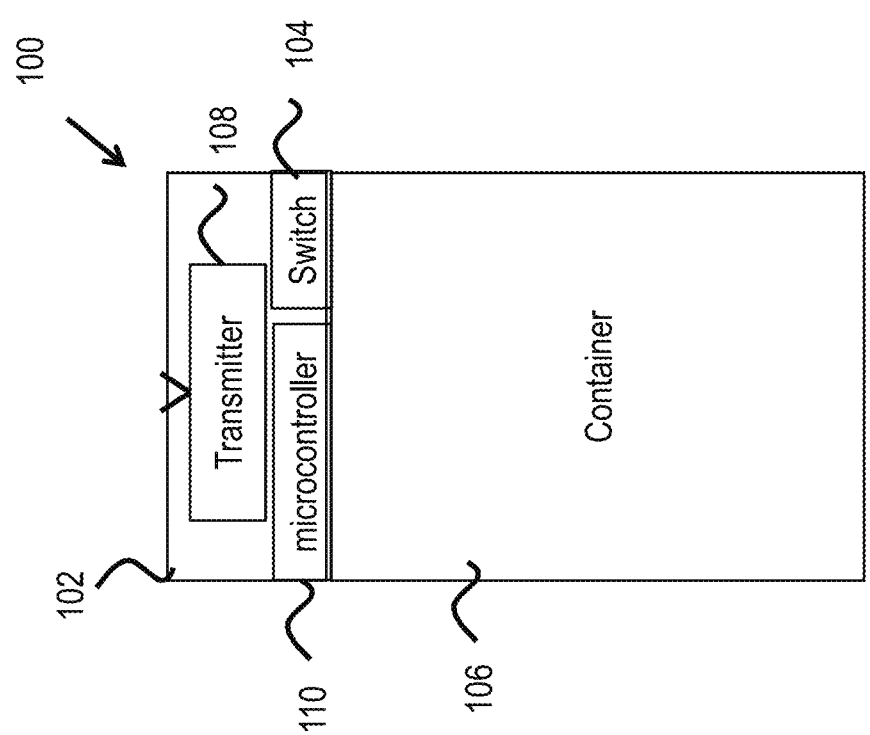
FIG. 2 is a block diagram of an implementation of a medication dispenser.

FIG. 2 shows an example embodiment of a pill bottle 100. The bottle 100 includes a cap 102 and a switch 104 that open or close access to a container area 106 in which pills or other form of medications can be stored. In some embodiments, the pill bottle 100 may be fitted to include a microcontroller 110. The microcontroller 110 may be a low power consuming processing unit and may contain nonvolatile embedded memory that may be used to transmit BLE beacons using a BLE beacon module. The transmission processing may be performed in a transmitter 108. The cap 102 may control access to the container 106 that holds medication, and therefore events of opening of the cap 102 may be associated with medication dispensing. The switch 104 may detect the opening or closing of the cap using a mechanism, such as a pressure sensing switch or a contact sensing switch. In some embodiments, the pill bottle 100 may be fitted with one or more lights such as a light emitting device (LED) which is not shown in FIG. 1. These LEDs may be used for user indication of pill consumption activity, as described herein.

In order to make the device most useful to users, the device should be able to provide some usage feedback. For example, if a user takes their medication at the correct time, the LED should indicate by flashing green. If a user has missed a dose, the LED might flash yellow, while multiple missed doses may be indicated by flashing red.

Some embodiments based on the disclosed techniques may implement an algorithm designed to recognize a medication regime without the need for manual programming. After establishing an estimated regime, these embodiments may collect validation data to confirm the usage pattern and subsequently adjust the behavior of its feedback mechanisms to fit the usage pattern.

Figure 3:
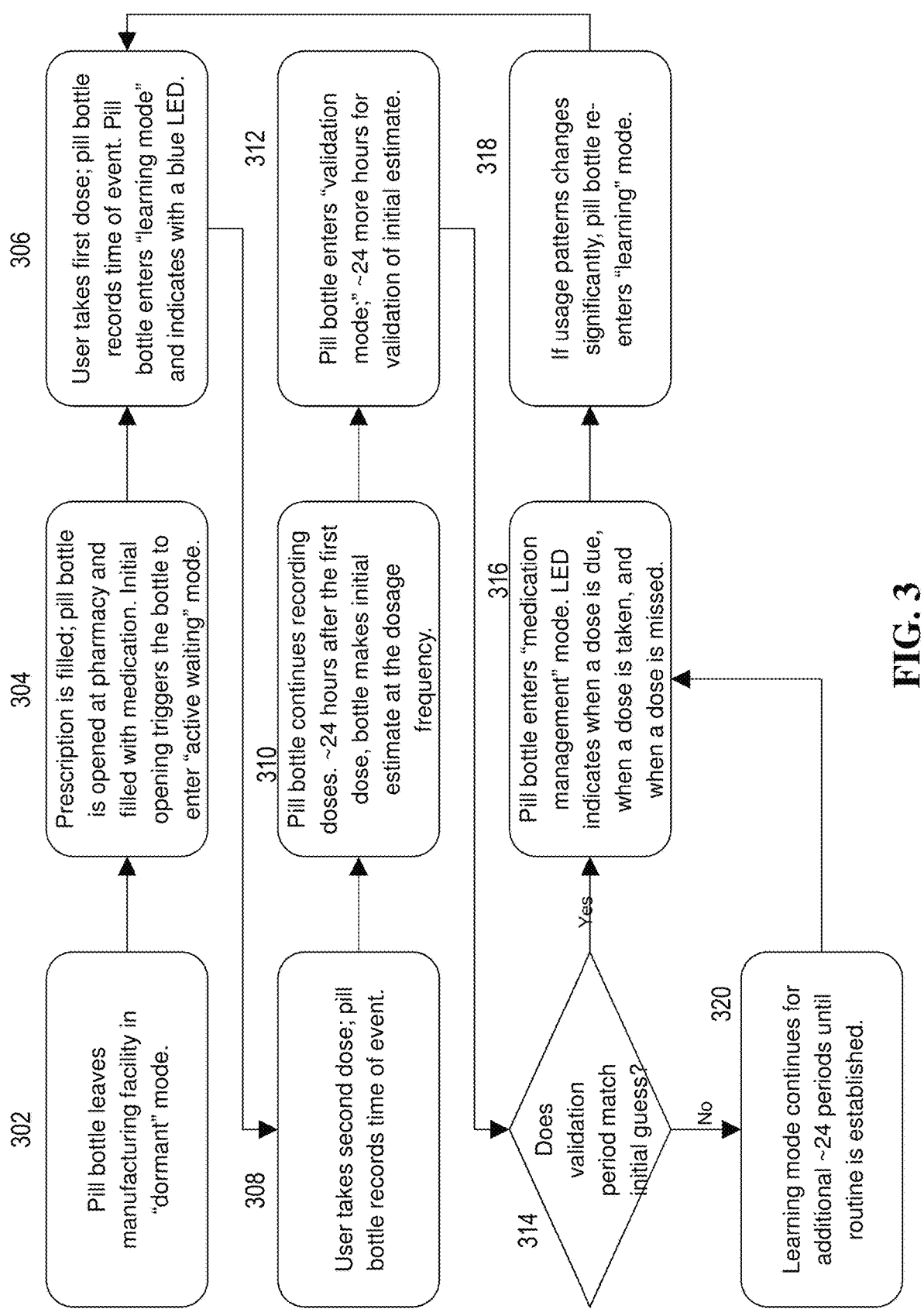
FIG. 3 is a flowchart of an example method of monitoring and reporting adherence to pill regimen.

FIG. 3 shows a flowchart of an example process 300 of learning medication schedule. At 302, a pill bottle may leave a manufacturing facility and be programmed in a dormant mode. At 304, a prescription is filled. During this step, the pill bottle is opened at a pharmacy and filled with medication. The pill bottle may be configured such that the initial opening triggers the bottle into an active waiting mode in which the bottle is ready to learn user's pill-taking behavior. At 306, the user may take (or dispense) his first dose. The pill bottle may record or log the time of the first medication dispensing using the cap opening event. At this time, the bottle enters a learning mode. This transition may be displayed on the display interface using a specific colored LED (e.g., blue) or by controlling the on/off or blinking pattern of the LED.

Subsequently, at 308, the user may take a second dose. The pill bottle may record the time of this event. At 310, the pill bottle may continue recording the medication dispensing events. The pill may stay in this learning mode for a predetermined duration, typically 1-day because medication is often prescribed with a per-day dose regimen.

After the learning mode duration is over, at 312, the pill bottle enters a mode of operation called validation. The pill bottle may stay in this mode for a second duration, at least 1-day or more, to verify that the regimen the pill bottle has learned appears to be accurate. During this time, the pill bottle display interface may be lit up to indicate that the pill bottle is in the validation mode.

After the pill bottle has collected sufficient medication dispensing data during the validation mode, the pill bottle may decide, at 314 whether the data collected during the validation period with the initially learned medication dispensing regime. When a match is detected at 314, the pill bottle may enter a medication management mode in which the pill bottle tracks medication dispensing and provides alerts when dose is due, a dose is taken or a dose is missed.

If a no-match condition is detected in step 314, then the pill bottle will continue learning (step 306) and after the learning mode duration, the pill bottle will begin medication management mode (Step 316). In the medication mode, if a significant deviation from the learned medication regime is detected, then the pill bottle may enter learning mode (step 306) once again.

In the above example embodiment, details such as the duration of the learning period, retraining, color and blink rates of LED's for different modes, etc. are all implementation details for a particular embodiment but do not alter the general concept.

Examples of Display Interface Embodiments

In order to make the device more useful to users, the device may to provide some usage feedback. A display interface may be used for the feedback. While a typical pill bottle cap can accommodate a small screen that can display alphanumeric display, to conserve battery life, a simple, more energy efficient and durable interface that includes one or more light emitting devices (LEDs) may be used. The display interface may be operates as follows: if a user takes their medication at the correct time, the LED should indicate by flashing green. If a user has missed a dose, the LED might flash yellow, while multiple missed doses may be indicated by flashing red. In some embodiments, a frequency of light blinks may be used to communicate the usage information. For example, slow blinking (e.g., once every 1 to 2 seconds) when a user is using medication per regimen, fast blink (e.g., more than once every second) when the user has missed some medication and either continuously on or rapid blinking (e.g., 5 or more times a second) to indicate that multiple doses have been missed.

Companion Device Examples

Once the algorithm has identified an estimated pattern/regime, it can transmit this information to a companion app informing the user of the schedule the pill bottle expects to follow. If this information is incorrect, the user could manually set the bottle back to "learning" mode (by pressing the button 5 times, for example).

Figure 4:
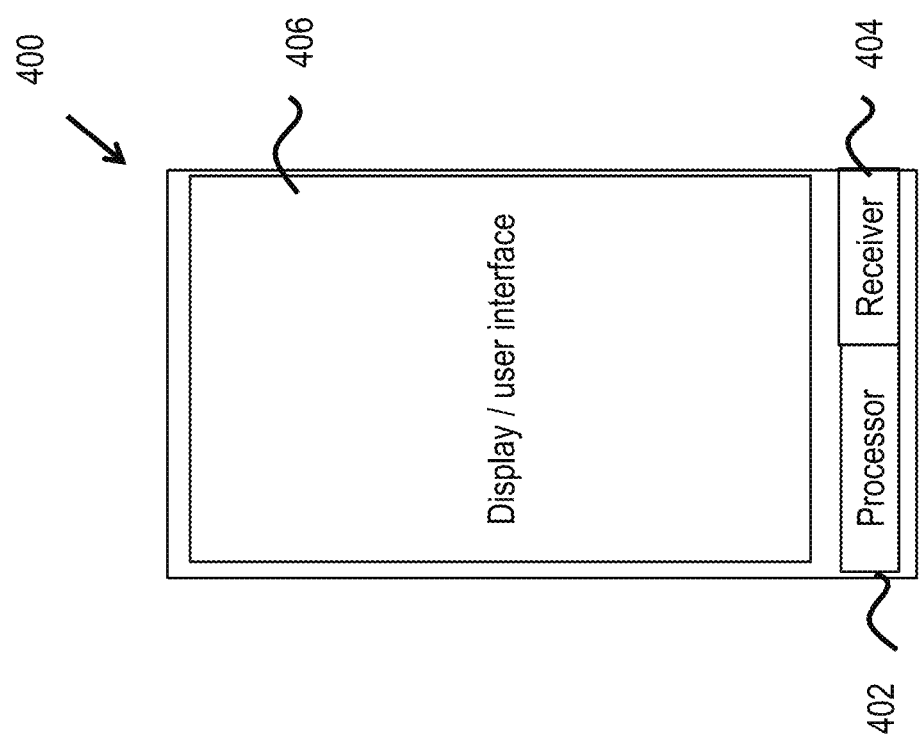
FIG. 4 shows an example user device that receives data from a medication dispenser.

FIG. 4 is a block diagram depiction of an example of a user device 400 that may be the companion device that receives information from the pill bottle. The device 400 includes a processor 402 and a receiver 404. For example, the receiver may be a BLE receiver or a Wi-Fi receiver, or another suitable wired or wireless receiver. The processor 402 may process data received by the receiver 404 and cause the data to be displayed on the display/user interface 406. The processor 402 may be configured to present the data in different ways such as graphs, charts, numbers, spreadsheets, color codes and so on. One notable feature of the user device 400 may be that, for the purpose of the medication regimen adherence, the user device 400 may only use its receiver 404, and may not perform any transmitting functions such as transmitting signals to the pill bottle.

In one advantageous aspect, enabling the pill bottle to learn the medication regime without the need to be programmed allows for the pill bottle hardware to be transmit only, substantially reducing the cost and complexity of the system and significantly increasing lifespan by reducing the power requirements.

In another advantageous aspect, a learning algorithm affords users the flexibility to set their own medication routine and habits (within the bounds of the medication requirements), giving them the flexibility to set a schedule that's easier to adhere to without being forced into a prescribed daily routine. This may positively affect adherence and usability.

In one example aspect, the learning algorithm has the potential to adapt to changing usage patterns over time without the need for reprogramming (e.g. if a user initially takes their daily medication every morning and switches to taking it before bed). This makes the quality of the feedback information (including medication reminders) more useful to the patient.

In another advantageous aspect, a learning algorithm reduces the burden on the pharmacy of programming each bottle with the prescription regimen.

Figure 5:
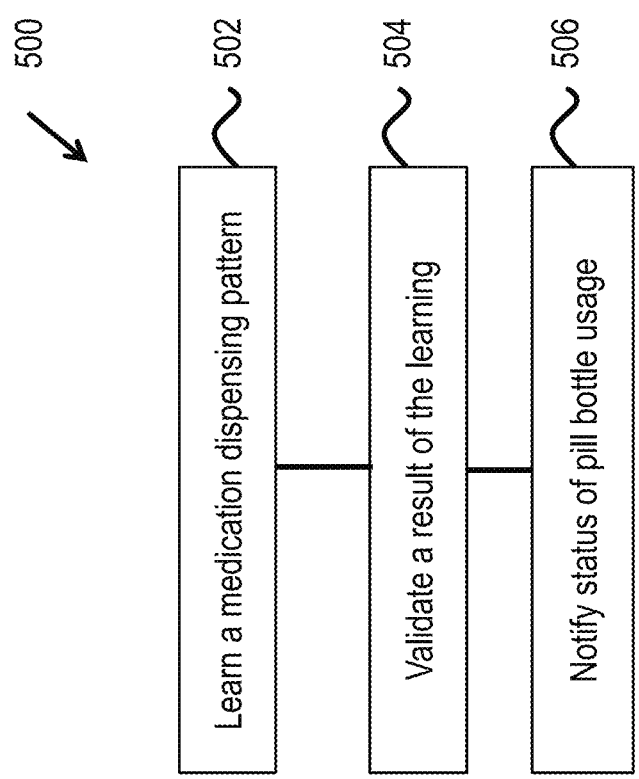
FIG. 5 is a flowchart of an example method of learning and monitoring a medication-taking regimen.

FIG. 5 shows a flowchart for an example method 500 implemented by a processor coupled to a pill bottle. For example, the processor may be located within the connectivity module shown in FIG. 1.

The method 500 includes, at 502, learning, during a first, or an initial, time period having a first duration, a medication dispensing pattern of a pill bottle.

The method 500 includes, at 504, validating, during a second time period having a second duration, a result of the learning.

The method 500 includes, at 506, notifying, during a third time period subsequent to the second time period, status of pill bottle usage with respect to the result of the learning.

In some embodiments, the learning operation (502) may start without any preprogrammed medication regime stored and accessible to the processor. For example, when a pill bottle with a connectivity module is shipped from the factor, there may not be any medication schedule programmed into it. In fact, the medication regimen may never be programmed into the pill bottle by an external entity at all. When a user picks up medication from the pharmacy, the medication regiment may be communicated to the user orally and/or via a label stuck to the pill bottle, but without programming the processor or connectivity module in the bottle cap. In some embodiments, the learning operation may start when the user opens the pill bottle the first time for taking a medication. In some embodiments, the learning operation may start when the pill bottle is opened at the pharmacy for filling the prescription. A mechanism such as a removable tab may optionally be included in the pill bottle so that the pharmacist can activate the connectivity module, which may be inactive (battery disconnected to conserve power) until then. In some embodiments, as described elsewhere in the present document, a user may be able to restart the learning operation by pressing keys or by removing and re-installing battery of the connectivity module.

The method 500 may be operated such that the learning operation 502 may be carried out for a day. This is because medications are often prescribed on a per-day basis. In alternate embodiments, the learning operation 502 may occur for longer (or shorter) durations and may be preconfigured by a manufacturer of the pill bottle. The validation period will typically run for at least as long as the learning period, to ensure that all user activity during the learning period is observed and compared at least once.

The notification operation 506 may include communicating the status of medication dispensing and compliance using one or the display technique described in the present document. For example, different colored LED lights may be used. For example, periodicity of light blinking may be used. For example, multiple LEDs representing multiple status will be used and an appropriate LED may be lit to communicate the status.

In some embodiments, an apparatus comprising a microprocessor may operate as follows. The microprocessor may run software code that causes the microprocessor to operate in a first state during which the microprocessor learns a medication dispensing regimen of a pill bottle (e.g., perform a learning operation), a second state during which the microprocessor validates the learned medication dispensing regimen using medication dispensing events of the pill bottle (e.g., performing a validation operation), and a third state during which the microprocessor indicates, on a display interface, a current status of usage in relation to the learned medication dispensing regimen (e.g., a notification operation). The processor may use a transmitter (no reception) to communicate the status messages, including historical data about medication regiment compliance to a companion device (e.g., as depicted in FIG. 4).

Examples of Learning Implementations

In some embodiments, the learning may be based on capturing times at which the user dispenses medications from the pill bottle. From the dispensing data, then an estimate may be made of the number of times a user takes the medication (e.g., twice during the day). From the dispensing data, an estimate may be made regarding spacing between the medication taking times. For example, it may be determined that the user is taking medication 6 hours apart. Another learning parameter may include relating the time medication is taken with time of day. For example, the learning process may conclude that the user took one tablet in the morning, and one tablet in the evening, spaced by 10 hours.

During validation period, an approximation window may be used. For example, the medication taking instances captured during the validation period may be considered to match the learned time when the validation times are within plus-minus N hours of the learned time (N may be for example 2 hours). A more stringent criterion may be used to compare the number of times medication is dispensed, for example even deviation of one instance may be considered to be non-matching with the learned regimen.

It will be appreciated that the present document provides techniques to improve the operation of a pill dispenser bottle, and in particular, a processor or a microcontroller that is affixed to a pill bottle. For example, the microcontroller is able to work in a transmit-only mode of operation in which the microcontroller does not receive any instructions or data from an outside source regarding a prescription filling. It will further be appreciated that the present document provides a technical solution that adapts to changes to a patient's medication routine. For example, when the learning algorithm senses a significant deviation (e.g., different amount of dosage taken for more than X days, where X is 2 to 5 days, such as a deviation in terms of how many times a medication is dispensed, where the deviation lasts for several days in a row) and automatically re-learns the changed medication routine.

Embodiments may also be described with reference to particular system configurations and networks. However, those skilled in the art will recognize that the features described herein are equally applicable to other system configurations, network types, etc. Moreover, the technology can be embodied as special-purpose hardware (e.g., circuitry), programmable circuitry appropriately programmed with software and/or firmware, or as a combination of special-purpose and programmable circuitry. Accordingly, embodiments may include a machine-readable medium having instructions that may be used to program a computing device to perform the methods described herein.

References in this description to "an embodiment" or "one embodiment" means that the particular feature, function, structure, or characteristic being described is included in at least one embodiment. Occurrences of such phrases do not necessarily refer to the same embodiment, nor are they necessarily referring to alternative embodiments that are mutually exclusive of one another.

Unless the context clearly requires otherwise, the words "comprise" and "comprising" are to be construed in an inclusive sense rather than an exclusive or exhaustive sense (i.e., in the sense of "including but not limited to"). The terms "connected," "coupled," or any variant thereof is intended to include any connection or coupling, either direct or indirect, between two or more elements. The coupling/connection can be physical, logical, or a combination thereof. For example, two devices may be communicatively coupled to one another despite not sharing a physical connection.

When used in reference to a list of multiple items, the word "or" is intended to cover all of the following interpretations: any of the items in the list, all of the items in the list, and any combination of items in the list.

It will be appreciated that this patent document discloses techniques for learning a user's medication dispensing habits by learning the habits, validating the habits and notifying compliance thereof.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

REMARKS

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling those skilled in the relevant art to understand the claimed subject matter, the various embodiments, and the various modifications that are suited to the particular uses contemplated.

Although the Detailed Description describes certain embodiments and the best mode contemplated, the technology can be practiced in many ways no matter how detailed the Detailed Description appears. Embodiments may vary considerably in their implementation details, while still being encompassed by the specification. Particular terminology used when describing certain features or aspects of various embodiments should not be taken to imply that the terminology is being redefined herein to be restricted to any specific characteristics, features, or aspects of the technology with which that terminology is associated. In general, the terms used in the following claims should not be construed to limit the technology to the specific embodiments disclosed in the specification, unless those terms are explicitly defined herein. Accordingly, the actual scope of the technology encompasses not only the disclosed embodiments, but also all equivalent ways of practicing or implementing the embodiments.

The language used in the specification has been principally selected for readability and instructional purposes. It may not have been selected to delineate or circumscribe the subject matter. It is therefore intended that the scope of the technology be limited not by this Detailed Description, but rather by any claims that issue on an application based hereon. Accordingly, the disclosure of various embodiments is intended to be illustrative, but not limiting, of the scope of the technology as set forth in the following claims.

The invention claimed is:
1. A medication dispenser apparatus, comprising:
a container configured to hold medication;
a display interface; and
a controller configured to perform, in sequence,
a learning operation in which the controller learns a medication dispensing regimen of the container over a first duration,
a validation operation in which the controller validates the learned medication dispensing regimen over a second duration that is greater than or equal to the first duration, and
a notification operation in which the controller provides on the display interface a status of use of the container for medication dispensing in relation to the learned medication dispensing regimen.

2. The medication dispenser apparatus of claim 1, wherein the controller is configured to perform the learning operation for the first duration after detecting occurrence of a start event.

3. The medication dispenser apparatus of claim 2, wherein the detecting occurrence of the start event includes detecting a medication filling event in which the container is filled with medication for a first time.

4. The medication dispenser apparatus of claim 2, wherein the detecting occurrence of the start event includes detecting that the status of use of the container for medication dispensing has deviated from the learned medication dispensing regimen.

5. The medication dispenser apparatus of claim 1, wherein the display interface includes at least one light emitting diode that emits light of at least one color.

6. The medication dispenser apparatus of claim 5, wherein the controller is configured to communicate the status of the use of the container via the display interface either by controlling which color is emitted by the at least one light emitting diode and/or by controlling a frequency of blinking of the at least one light emitting diode.

7. The medication dispensing apparatus of claim 1, wherein the controller is configured to begin the learning operation again when the controller decides during the notification operation that the learned medication dispensing regimen is not being followed.

8. A processor-implemented method, comprising:
   learning, during a first time period having a first duration, a medication dispensing pattern of a pill bottle;
   validating, during a second time period having a second duration that is at least as long as the first duration, a result of the learning; and
   notifying, during a third time period subsequent to the second time period, status of pill bottle usage with respect to the result of the learning.

9. The method of claim 8, wherein the learning starts without any preprogrammed medication dispensing pattern.

10. The method of claim 8, wherein the learning starts upon receiving a user input at an interface of the pill bottle.

11. The method of claim 8, wherein the first duration is 24 hours.

12. The method of claim 8, wherein the notifying includes indicating status by emitting a color representing of the status.

13. The method of claim 8, wherein the notifying includes blinking a light at a frequency corresponding to the status.

14. The method of claim 8, wherein the notifying includes displaying at least one alphanumeric character indicative of the status.

15. An apparatus comprising a microprocessor configured to operate in:
   a first state during which the microprocessor learns a medication dispensing regimen of a pill bottle over a first interval of time;
   a second state during which the microprocessor validates the learned medication dispensing regimen using medication dispensing events of the pill bottle over a second interval of time that is at least as long as the first interval of time; and
   a third state during which the microprocessor indicates, on a display interface, a current status of usage in relation to the learned medication dispensing regimen.

16. The apparatus of claim 15, wherein the microprocessor is further configured to transmit data related to the medication dispensing events and the current status using a wireless communication transmitter.

* * * * *